United States Patent
Jansen et al.

(10) Patent No.: US 8,496,939 B2
(45) Date of Patent: Jul. 30, 2013

(54) INJECTABLE WATER-IN-OIL EMULSIONS

(75) Inventors: Theodorus Jansen, Venray (NL); Virgil Elisabeth Joseph Caspar Schijns, Nijmegen (NL); Erik Hermkens, Handel (NL)

(73) Assignee: Intervet International B.V., Boxmeer (NL)

( * ) Notice: Subject to any disclaimer, the term of this patent is extended or adjusted under 35 U.S.C. 154(b) by 2059 days.

(21) Appl. No.: 10/469,391

(22) PCT Filed: Feb. 26, 2002

(86) PCT No.: PCT/EP02/02145
§ 371 (c)(1),
(2), (4) Date: Aug. 28, 2003

(87) PCT Pub. No.: WO02/067899
PCT Pub. Date: Sep. 6, 2002

(65) Prior Publication Data
US 2004/0071716 A1    Apr. 15, 2004

(30) Foreign Application Priority Data
Feb. 28, 2001 (EP) .................... 01200745

(51) Int. Cl.
*A61K 39/00* (2006.01)
*A61K 39/38* (2006.01)

(52) U.S. Cl.
USPC ......................... 424/184.1; 424/400

(58) Field of Classification Search
None
See application file for complete search history.

(56) References Cited

U.S. PATENT DOCUMENTS

| | | | | |
|---|---|---|---|---|
| 4,203,877 A * | 5/1980 | Baker | ............ | 524/500 |
| 4,806,350 A * | 2/1989 | Gerber | ............ | 424/198.1 |
| 4,963,656 A * | 10/1990 | Mitani | ............ | 530/353 |
| 5,118,698 A * | 6/1992 | Fries | ............ | 514/359 |
| 5,622,649 A * | 4/1997 | Hunter et al. | ............ | 516/29 |
| 5,635,163 A * | 6/1997 | Hansenne | ............ | 424/60 |
| 5,646,212 A * | 7/1997 | Hibbert | ............ | 524/500 |
| 5,885,590 A * | 3/1999 | Hunter et al. | ............ | 424/280.1 |
| 5,935,589 A * | 8/1999 | Mukherjee et al. | ............ | 424/401 |
| 6,099,829 A | 8/2000 | Schehlmann et al. | | |
| 6,174,518 B1 * | 1/2001 | Allard | ............ | 424/59 |
| 6,174,846 B1 * | 1/2001 | Villa | ............ | 510/159 |
| 6,235,282 B1 * | 5/2001 | Riviere et al. | ............ | 424/184.1 |
| 6,451,325 B1 * | 9/2002 | Van Nest et al. | ............ | 424/283.1 |
| 2003/0083231 A1 * | 5/2003 | Ahlem et al. | ............ | 514/2 |
| 2006/0188463 A1 * | 8/2006 | Kim et al. | ............ | 424/70.13 |

FOREIGN PATENT DOCUMENTS

| | | | |
|---|---|---|---|
| WO | WO 9607689 | * | 3/1996 |
| WO | 00 33806 | | 6/2000 |

OTHER PUBLICATIONS

Cox, John C. et al: "Adjuvants—a classification and review of their modes of action": VACCINE (1997), 15(3), pp. 248-256.
Tadros, T.F. et al: "Stabile W/O-UND W/O/W—Emulsionen Mit Polymeren Tensiden"; Parfumerie Und Kosmetik, Heuthig, Heidelberg, DE, vol. 78, No. 4, Apr. 1997, pp. 30-34.
Gupta R.K. et al: "Adjuvants for human vaccines—current status, problems and future prospects"; Vaccine, Butterworth Scientific. Guildford, GB, vol. 13, No. 14, Oct. 1, 1995, pp. 1263-1276.

* cited by examiner

*Primary Examiner* — Rachael E Bredefeld

(57) ABSTRACT

Personal care or cosmetic oil in water emulsions include an oil emulsifier and a combination of a Xanthan polysaccharide and a polyglucomannan polysaccharide to provide enhanced stability even at low emulsifier stabilizer levels. The emulsifier stabilizer system provides stable emulsions without dominating system rheology, particularly viscosity. Thus, the emulsions can have a low viscosity suitable for formulation as milks or thin lotions, or can be thickened, desirably by thickening agents other than the Xanthans and/or polyglucomannan, to provide emulsion creams or gels. This enables the system to be used very flexibly in end use applications. The emulsifier is desirably a non-ionic emulsifier and particularly is a combination of a low HLB and a high HLB emulsifier and can be formulated with conventional alcohol ethoxylate surfactants or from non-EO surfactants e.g. sucrose ester high HLB surfactants and citrate or sorbitan ester low HLB surfactants.

13 Claims, No Drawings

INJECTABLE WATER-IN-OIL EMULSIONS

This application is a National Stage of International Application No. PCT/EP02/02145, filed Feb. 26, 2002, which relies for priority on European Application EPO/01200745.6 filed Feb. 28, 2001.

The present invention relates to adjuvants comprising water-in-oil emulsions, a method to prepare these emulsions, and vaccines comprising the adjuvants.

Water-in-oil (w/o) emulsions are two phase systems consisting of a continuous oil phase and an aqueous phase (discontinuous phase) whereby the aqueous phase is dispersed as small droplets in the oil phase, and one or more surfactants and emulsifiers. W/o emulsions are widely applied in medicine, cosmetics and the food and beverage industry. In medicine w/o emulsions are generally used in pharmaceutical formulations as vehicle of therapeutic agents, especially in case of water-insoluble or water-sensitive active ingredients. In vaccination, w/o emulsions are commonly used as adjuvant to stimulate the immune response against target antigens derived from one or more infectious agent(s). One of the oldest w/o emulsion adjuvant is Freund's Complete Adjuvant (FCA) containing mycobacteria in mineral oil and ARLACEL A® as surfactant or Freund's Incomplete Adjuvant, which lacks the mycobacteria. Other w/o emulsions of mineral or metabolisable oils have been developed and are regularly used as adjuvant in vaccination.

W/o emulsions are generally applied via injection. To be injectable a composition must be substantially fluid. However the w/o emulsions are often relatively viscous which makes injection of these emulsions very difficult. Especially with w/o emulsions of metabolisable oils the viscosity is a problem.

In w/o emulsions, the viscosity in general is dependent on the viscosity of the continuous phase, that is the oil phase. Different oils can be used in adjuvants, both mineral and non-mineral (metabolisable) oils. However, although oil based adjuvants generally increase the immunological activity of the vaccines, compared to non-oily vaccines, they can cause local reactions at the injection sites of the vaccines, especially when mineral oils are used. This may be caused by the fact that mineral oils cannot be metabolised by the vaccinated organism and tend to stay close to the injection sites.

In view of the problem of local reactions at the injection site, the replacement of mineral oils by non-mineral, metabolisable, oils would be desirable. However, the immunogenic activity of the adjuvant should remain high, when using the mineral oil instead of the non-mineral oil. Preferably, the immunogenic activity of adjuvants based on metabolisable oils should be as high as for the adjuvants based on mineral oils, while the problem of local tolerance is virtually absent. Moreover, the adjuvants based on w/o emulsion on the basis of non-mineral oil should be stable, and should have an acceptable shelf life.

However, metabolisable oils, and in particular (semi-) synthetic- and vegetable oils are viscous at room temperature and their use in w/o emulsions leads to emulsion viscosity's that are similar to that of the individual oil. A reduction of the oil content (and consequently an increase in the water content) however often causes an increase in the emulsion viscosity to such an extent that injection is no longer possible. Besides an effect on the viscosity, changes in the oil content of a w/o emulsion effect the stability of the emulsion. Reduction of the oil content results in an enlarged interfacial area. The quantity of emulsifier (dependant on the size of the interfacial area) will be insufficient and the emulsion will break.

The size of the interfacial area is also dependant on the droplet size of the dispersed phase: a reduced droplet size results in an enlarged interfacial area. Mechanical means can be used to reduce or increase the droplet size of the dispersed phase. Compared to high shear processing equipment, low shear processing results in increased droplet size and, therefore, reduced interfacial area.

These limitations make it difficult to obtain stable and fluid w/o emulsions, especially when based on metabolisable oils. Hence there is a need to find other methods and/or means to obtain stable w/o emulsions, which at the same time are fluid. The present invention aims to provide adjuvants based on stable w/o emulsions that are very suitable for injection, even when metabolisable oils are used, and have a good adjuvant activity.

Surprisingly it has been found that when certain specific emulsifiers are used w/o emulsions can be made that are stable, and provide excellent adjuvant activity, even when based on non-mineral, metabolisable oils. The emulsions have a very low viscosity and thus suitable for injection.

The present invention therefore provides adjuvant, for use in vaccine formulation, comprising a water-in-oil emulsion, characterised in that said emulsion comprises a polymeric emulsifier which is a block copolymer having a general formula A-COO-B-OOC-A, in which B is the divalent residue of a water-soluble polyalkylene glycol and A is the residue of an oil-soluble complex monocarboxylic acid. Such polymeric emulsifiers, as well as the preparation thereof, have been disclosed in GB 2002400 and WO9607689, the contents of which are herewith incorporated by reference. The emulsifiers, as described in GB 2002400, are emulsifiers wherein A has a molecular weight of at least 500 and is the residue of an oil-soluble complex mononcarboxylic acid, i.e. a fatty acid. These complex monocarboxylic acids may be represented by the general formula:

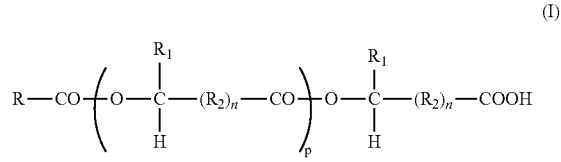

(I)

in which
R is hydrogen or a monovalent hydrocarbon or substituted hydrocarbon group;
$R_1$ is hydrogen or a monovalent $C_1$ to $C_{24}$ hydrocarbon group;
$R_2$ is a divalent $C_1$ to $C_{24}$ hydrocarbon group;
n is zero or 1;
p is an integer from zero to 200.

The units between the brackets in formula 1 may be all the same or they may differ in respect of $R_1$, R2 and n. The quantity p will not normally have the same unique value for all molecules of the complex acid but will be statistically distributed about an average value lying within the range stated, as is commonplace in polymeric materials. Polymeric component B has a molecular weight of at least 500 and is the divalent residue of a water-soluble polyalkylene glycol having the general formula

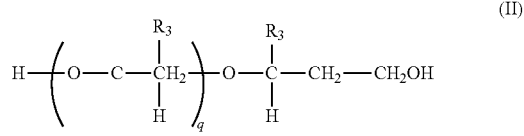

(II)

wherein
$R_3$ is hydrogen or a $C_1$ to $C_3$ alkyl group;
q is an integer from 10 up to 500.

The repetitive units in formula II again may all be the same or may differ in $R_3$, and the quantity q may vary about an average value.

The hydrocarbons R, $R_1$, and $R_2$ may be linear or branched. Preferably in the block copolymers of formula A-COO-B-OOC-A, component B is derived from polyethylene glycol and components A are derived from stearic acid, for example polyhydroxystearic acid, preferably from poly (12-hydroxystearic acid).

Thus, R may be a straight chain $C_{17}H_{35}$-group derived from stearic acid, and the unit containing $R_1$ and $R_2$ may be derived from 12-hydroxy-stearic acid.

p, in this case, preferably has a value of at least 2.

Preferably q may have a value between 20 and 60, more preferably above 23.

The weight ratio of the combined components A to the component B may vary widely, and typically will lie in the range from 9:1 to 1:9.

Most preferred emulsifiers used in the adjuvants according to the invention are ARLACEL P135, a PEG 30 Dipolyhydroxystearate. Another, similar, emulsifier for use with the invention is ATLOX®4912. Both ARLACEL P135 and ATLOX®4912 are block copolymers (A-B-A) of polyethylene glycol and polyhydroxystearic acid with a mol weight of approximately 5000 commercially available from ICI.

These polymeric block copolymers were found to be compatible with a wide variety of oils, thus providing a much wider range of w/o emulsions having the required stability and fluidity to ensure administration via injection, and which are very well tolerated by the vaccinated subjects. Furthermore the use of these ABA type block copolymers lead to w/o emulsions having excellent stability during storage thus improving the shelf life of said emulsions. The resulting w/o emulsions were stable and fluid at low temperatures, especially at 25° C.

Most important, the adjuvants according to the invention, based on the use of the above-mentioned ABA block copolymer type emulsifiers surprisingly had excellent immunostimulating (adjuvant) activity when used in vaccines, while no local reactions at the injection site were induced.

The w/o emulsions according to the invention may comprise 0.01-15% w/w, preferably 0.05-10% w/w, more preferably 0.1-3% w/w, most preferably 0.3-0.5% w/w of the polymeric emulsifier according to the invention. In a most preferred embodiment a w/o emulsions according to the invention comprises 0.5% w/w of the polymeric emulsifier according to the invention. If necessary, other emulsifiers may also be used in addition to the polymeric emulsifier according to the invention in the w/o emulsion according to the invention.

The w/o emulsions according to the invention may comprise 30-90%, preferably 35-60%, more preferably 40-60% by weight of oil.

Suitable oils for use in a w/o emulsion according to the present invention are non-metabolisable oils, metabolisable oils and mixtures of metabolisable and non-metabolisable oils. Non metabolisable oils that can be used in the adjuvants according to the invention include but are not limited to mineral oils and paraffin oils.

Metabolisable oils according to the invention include but are not limited to vegetable oils, animal oils, natural hydrocarbons, metabolisable synthetic or semi-synthetic oils (such as Miglyol and Cetiol), fatty acid esters of propylene glycol and C6 to C24 fatty acids such as oleyl oleates, diesters of capric- or caprylic acids and the like. Suitable vegetable oils are peanut oil, soybean oil, sunflower oil, and the like. Suitable animal oils are squalane and squalene and the like.

Preferably the oil phase is metabolisable oil or a mixture of metabolisable oils, since non-metabolisable oils (mineral oils) tend to give local reactions at the injection sites. Preferred oils are the semi-synthetic oils such as Mygliol and Cetiol and oleyl oleates, esters of oleic ester, preferably ethyloleate.

With the adjuvants according to the invention very low viscosities can be reached and the emulsions are stable, while good adjuvant activity is obtained and no local reactions at the injection site occur.

The adjuvant according to the invention preferably comprises w/o emulsions having a viscosity below 450 mPa·s, preferably less than 250 mPa·s, more preferably less than 100 mPa·s when tested in a Brookfield DV-I+ viscometer utilising spindle type No. 62 for 30 sec. at 60 r.p.m.

The aqueous phase of the w/o emulsions according to the present invention is usually made up of water, saline or buffer, such as phosphate buffered saline.

The adjuvant according to the invention can be used in vaccines. The vaccine will usually comprise antigenic material of an infectious agent. Vaccines comprising said adjuvants and an antigenic component derived from an infectious agent are likewise part of the present invention. Vaccines according to the invention may comprise the antigenic component in the discontinuous aqueous phase of the emulsion.

The use of a polymeric emulsifier which is a block copolymer having a general formula A-COOB-OOC-A, in which B is the divalent residue of a water-soluble polyalkylene glycol and A is the residue of a oil-soluble complex monocarboxylic add in the preparation of an adjuvant for use in a vaccine, and the use of these emulsifiers in vaccines is likewise part of the present invention.

Trough vaccination the immune system is triggered, resulting in a protective immune response against the infectious agent. Vaccines may be based on living, attenuated microorganisms, or killed (inactivated) microorganisms, as well as on subunits of microorganisms as antigenic component. Especially in the case of inactivated or sub-unit vaccines, an adjuvant is used to increase the immune response.

The antigenic material may be mixed with the adjuvant. In the vaccine the antigenic material may be present in the discontinuous water phase of the adjuvant as added. The vaccine preparations based on an adjuvant according to the invention can be prepared according to methods known in the art.

The w/o emulsions for use in the adjuvants according to the present invention can be used to prepare water-in-oil-in-water (w/o/w) emulsions based on droplets of the aforementioned w/o emulsion in an external aqueous phase. The w/o and w/o/w emulsions according to the present invention are suitable for use as adjuvant in vaccines, especially veterinary vaccines. Moreover, the w/o emulsions according to the present invention are suitable for use as vehicle for therapeutical agents, especially water-insoluble or water-sensitive active ingredients, and nutritious supplements. Thus in a further aspect the present invention provides for pharmaceutical compositions based on a w/o- or w/o/w emulsion according to the present invention.

The emulsions according to the invention can be prepared using standard techniques. In general the aqueous phase, the oil phase, the polymeric emulsifier according to the invention and optionally other emulsifiers are brought together and emulsified until a stable emulsion having the desired low viscosity is obtained. When emulsions are prepared, energy must be expended to form an interface between the oily and aqueous phases. Therefore, emulsification equipment includes a wide variety of agitators, homogenisers, colloid mills, jet mixers and ultrasonic devices. Production-size agitators can be propeller shaped or paddle shaped stirring systems, with rotation speed usually up to 2000 r.p.m., that are considered as low shear mixing procedures. Another type of production-site agitator is the colloid mill. The principle of operation of the colloid mill is the passage of the mixed phases of an emulsion formula between a stator and a high-speed rotor revolving at speeds of 2000 to 18000 rpm that is considered as a high shear mixing procedure.

Water-in-oil emulsions can be processed into a water-in-oil-in-water emulsion (also called "double emulsion"), where the internal and external aqueous phases are separated by an oil phase. This process consists of mixing the water-in-oil emulsion into an aqueous phase containing the proper emulsifying agent. In these systems both hydrophobic and hydrophilic emulsifier are used to stabilize the double emulsion.

The polymeric emulsifier according to the invention is preferably dissolved in the oil phase. Additional emulsifiers may be incorporated in the aqueous phase or oil phase.

In case of a w/o/w emulsion, a w/o emulsion according to the invention is prepared as primary w/o emulsion, which is subsequently added to a second aqueous phase and a second emulsifier and homogenised to obtain the desired w/o/w emulsion. The second emulsifier required to make the w/o/w emulsion is preferably an emulsifier with an HLB of 10-18, or a combination of two or more emulsifiers so that a desired HLB is obtained. Details concerning the manufacture of pharmaceutical emulsions can be found, for example in: "The Theory And Practice Of Industrial Pharmacy" (Eds: Lachman L. et al, Lea & Febiger, Philadelphia, USA, 1970, Chapter 16), and "Remington's Pharmaceutical Sciences" (Eds: Gennaro, A. R. Mack Publishing Company, Easton, USA, 1990, 18$^{th}$ edition).

The vaccines according to the invention are preferably administered parenteral, e.g. intramuscularly, subcutaneous or intravenous. However if necessary the vaccines can also be administered non-parental e.g. per os, spraying, i.o. drops or intranasal drops. The low viscosities of the emulsions used in the adjuvants and/or vaccines of the present invention are extremely suitable for parenteral administration.

The following examples are merely to demonstrate the invention without limiting the invention to the particular embodiments.

EXAMPLES

Example 1

A water-in-oil emulsion containing the inactivated antigens of Infectious Bronchitis virus, strain Massachusetts and New Castle Disease virus, strain clone 30 are manufactured with a water/oil ratio of 50/50% w/w. Besides the antigens, the water phase contains 0.01 m PBS. The organic phase contains a Medium Chained Triglyceride (MIGLYOL 840) and 3% w/w PEG-30 Dipolyhydroxystearate (Arlacel P135) as emulsifier. ARLACEL P135 is dissolved in MIGLYOL 840 at 60° C. while stirring. After dissolution this oil phase is cooled down to room temperature. The water phase is added slowly to this oil phase under high shear homogenisation using an Ultra Turrax type of homogeniser. The resulting water droplets have a size of mainly 1 µm. The viscosity of this emulsion is 115 mPa·s at 25° C. and showed sufficient stability in an accelerated stability test based on storage at 37° C. during three weeks.

Example 2

A water-in-oil emulsion containing the inactivated antigens of Infectious Bronchitis virus, strain Massachusetts and New Castle Disease virus, strain clone 30 are manufactured with a water/oil ratio of 70/30% w/w. Besides the antigens, the water phase contains 0.01 m PBS. The organic phase contains a Medium Chained Triglyceride (Miglyol 840); 3% w/w PEG-30 Dipolyhydroxystearate (ARLACEL P135) as emulsifier. ARLACEL P135 is dissolved in MIGLYOL 840 at 60° C. while stirring. After dissolution this oil phase is cooled down to room temperature. The water phase is added slowly to this oil phase while stirring at 1100 r.p.m. using an IKA Eurostar mixer. The resulting water droplets have a size of mainly between 1 and 5 µm. The viscosity of this emulsion is 424 mPa·s at 25° C. and showed sufficient stability in an accelerated stability test based on storage at 37° C. during three weeks. Three-week-old SPF female chicken, vaccinated intramuscularly once with 0.5 ml of this vaccine showed a mean 2 log HI-IBV serum titre of 7.0 and a mean 2 log HI-NDV serum titre of 4.4, nine weeks after vaccination.

Example 3

A water-in-oil-in-water emulsion is prepared using as emulsifiers: PEG-30 Dipolyhydroxystearate ARLACEL P135 and SYNPERONIC F127. The primary water-in-oil emulsion is based on a water/oil ratio of 60/40% w/w. The water phase contains the inactivated antigens of Infectious Bronchitis virus, strain Massachusetts and New Castle Disease virus, strain clone 30. Besides the antigens, the water phase contains 0.01 m PBS. The organic phase contains a Medium Chained Triglyceride (MIGLYOL 840) and 3% w/w ARLACEL P135 as emulsifier. ARLACEL P135 is dissolved in MIGLYOL 840 at 60° C. while stirring. After dissolution this oil phase is cooled down to room temperature. The water phase is added slowly to this oil phase under high shear homogenisation using an Ultra Turrax type of homogeniser. The resulting water droplets have a size of mainly between 1 and 5 µm. The secondary emulsion is based on a water-in-oil/water of 60/40% w/w. The external water phase contains besides 0.01 m PBS also 3% w/w SYNPERONIC F127. The water-in-oil emulsion is added slowly to this water phase under mediate shear (16.000 r.p.m.) homogenisation using an Ultra Turrax type of homogeniser. The resulting water-in-oil droplets have a size of mainly between 1 and 5 µm. The viscosity of this W/O/W emulsion is 110 mPa·s at 25° C. and showed stability for at least 6 months at 2-8° C.

Example 4

A water-in-oil emulsion containing the inactivated antigens of Infectious Bronchitis virus, strain Massachusetts and New Castle Disease virus, strain clone 30, is manufactured with a water/oil ratio of 40/60% w/w. Besides the antigens, the water phase contains 0.01 m PBS. The organic phase contains Ethyloleate and 0.1% w/w PEG-30 Dipolyhydroxystearate (Arlacel P135) as emulsifier. Arlacel P135 is dissolved in at 60° C. while stirring. After dissolution this oil phase is cooled down to room temperature. The water phase is mixed into this oil phase while stirring at 1300 r.p.m. during 5 minutes using an IKA Eurostar mixer. The resulting water droplets have a size of mainly between 1 and 5 µm. The viscosity of this emulsion is 25 mPa·s at 25° C. and showed sufficient stability in an accelerated stability test based on storage at 37° C. during three weeks.

Example 5

Water-in-Oil Formulation with Low Amounts of ARLACEL P135

A water-in-oil emulsion is manufactured with a water/oil ratio of 60/40% w/w. The water phase contains 0.01 m isotonic Phosphate buffer. The organic phase contains a Medium Chained Triglyceride (MIGLYOL 840) and 0.5% w/w PEG-30 Dipolyhydroxystearate (ARLACEL P135) as emulsifier. ARLACEL P135 is dissolved in MIGLYOL 840 at 60° C. while stirring. After dissolution this oil phase is cooled down to room temperature. The water phase is added to this oil phase while stirring at 1100 r.p.m. during 5 minutes using an IKA Eurostar mixer. The resulting water droplets have a size of mainly between 1 and 5 μm. The viscosity of this emulsion is 127 mPa·s at 25° C. and showed sufficient stability in an accelerated stability test based on storage at 37° C. during three weeks.

Example 6

A water-in-oil emulsion containing the inactivated antigens of Infectious Bronchitis virus, strain Massachusetts and New Castle Disease virus, strain done 30 is manufactured with a water/oil ratio of 40/60% w/w. Besides the antigens, the water phase contains 0.01 m PBS. The organic phase contains Propyleneglycol Dicaprylcaprate and 0.1% w/w PEG-30 Dipolyhydroxy-stearate (Arlacel P135) as emulsifier. Arlacel P135 is dissolved in Propyleneglycol Dicaprylcaprate at 60° C. while stirring. After dissolution this oil phase is cooled down to room temperature. The water phase is mixed into this oil phase while stirring at 1300 r.p.m. during 5 minutes using an IKA Eurostar mixer. The resulting water droplets have a size of mainly between 1 and 5 μm. The viscosity of this emulsion is 35 mPa·s at 25° C. and showed sufficient stability in an accelerated stability test based on storage at 37° C. during three weeks.

Example 7

Variation Types of Oil

Materials
Mineral Oil (MARCOL 52 from Exxon, USA), EUTANOL G (Fatty alcohol from Henkel, Germany), CETIOL PGL (Hexyldecanol/Hexyldecyl Laurate from Henkel, Germany) and Isopropylmyristate (Merck, Germany), ESTOL 1526 (Medium Chained Triglyceride from Unichema, Spain) and Ethyloleate (AKZO-Nobel Chemicals, Sweden) are the types of oil tested. The ethyloleate and ESTOL 1526 used in this example, and in the following examples 8 and 9, contained 7.5% w/w vitamin E acetate. ARLACEL P135 (ICI, UK) in a concentration of 0.25% w/w (unless otherwise indicated) was used as surfactant. ARLACEL P135 was mixed into the oil phase while heating it up to 60° C.

Type of formalin-inactivated viral avian antigen tested: New Castle Disease Virus (NDV), strain Clone 30 (produced in eggs). The total concentration of virus suspension used was 8% w/v of the final vaccine. The aqueous phase, containing the virus suspension was diluted with 0.01 M Phosphate buffer, pH=7.2.

Preparation of the Emulsions

Two types of preparations were tested. For low shear emulsions mixing of the aqueous phase into the oil phase was performed at 1100-1300 r.p.m. using the Eurostar mixer (IKA, Germany) provided with a propeller blade. For high shear emulsions, mixing was performed with high shear forces at 20.000 r.p.m. using the Ultra Turrax Type T25 (IKA, Germany). Variations of the water/oil ratios tested were 60/40 and 30/70 (all in % w/w). The droplet size of the emulsion was determined using interference microscopy at 1000× magnification (Olympus, model BX50, Japan). Droplet size of the emulsions prepared under low shear conditions were mainly 1-5 μm, while emulsions prepared under high shear conditions were mainly about 1 μm. Accelerated physical stability tests were performed by determining the appearance after storing the emulsions at 37° C. during three weeks. None of the samples tested showed emulsion breakdown after three weeks at 37° C.

Immunization of Animals

Groups of three week-old specific pathogen free (SPF) female chickens (n=8-10) were vaccinated intramuscularly with 0.5 ml of the vaccines, in the breast muscle. Blood samples for serological tests were taken on weeks 3, 6, 9 and 12 after vaccination. Virus haemagglutination inhibition (HI) tests for ND were performed to determine the levels of antiviral serum antibody titers.

Serum levels of NDV-specific antibodies were determined by haemagglutination inhibition assay. Serial two-fold serum dilutions were prepared in microtiter plates and mixed with an equal volume containing 8 haemagglutinating units/50 μl NDV antigen. Titers were expressed as the reciprocal of the highest dilution that gives complete inhibition of haemagglutination. Samples were regarded to be positive at an inhibition of haemagglutination at dilution $\geq$1:2.

Results are shown in the following table.

| | | Results | | | | |
|---|---|---|---|---|---|---|
| TYPE OF OIL | WATER/OIL RATIO (% w/w) | EMULSIFICATION PROCESS | 2LOG HI TITERS NDV | | | |
| | | | 3 WKS | 6 WKS | 9 WKS | 12 WKS |
| EUTANOL G | 30/70 | Low shear | 9.5 | 7.8 | 6.6 | 6.5 |
| EUTANOL G | 30/70 | High shear | 9.2 | 8.0 | 6.7 | 6.5 |
| EUTANOL G | 60/40 | Low shear | 10.1 | 8.3 | 7.3 | 6.9 |
| Isopropylmyristate | 30/70 | Low shear | 6.1 | 5.3 | 4.8 | 4.7 |
| Isopropylmyristate | 30/70 | High shear | 5.8 | 6.1 | 4.1 | 4.9 |
| Isopropylmyristate | 60/40 | Low shear | 6.5 | 6.1 | 4.8 | 4.8 |
| Isopropylmyristate | 60/40 | High shear | 4.0 | 4.0 | 2.9 | 2.7 |
| CETIOL PGL | 30/70 | Low shear | 7.8 | 6.7 | 5.8 | 5.1 |
| CETIOL PGL | 30/70 | High shear | 8.4 | 7.5 | 6.7 | 6.2 |
| CETIOL PGL | 60/40 | Low shear | 6.9 | 6.9 | 6.0 | 5.2 |
| CETIOL PGL | 60/40 | High shear | 6.0 | 6.4 | 5.8 | 5.4 |
| Mineral Oil | 30/70 | Low shear | 8.8 | 9.7 | 9.2 | 8.1 |
| Mineral Oil | 30/70 | High shear | 9.3 | 9.2 | 8.8 | 8.9 |
| Mineral Oil | 60/40 | Low shear | 9.5 | 9.7 | 9.5 | 9.5 |
| Mineral Oil | 60/40 | High shear | 8.9 | 9.9 | 8.9 | 8.7 |
| Ethyloleate | 40/60 * | Low shear | 9.7 | 8.4 | 7.1 | 6.9 |
| ESTOL 1526 | 40/60 * | Low shear | 9.3 | 8.9 | 5.4 | 6.2 |

* Amount of ARLACEL P135 = 0.1 % w/w

Example 8

Variation Water-Oil Ratio

Materials

Ethyloleate (AKZO-Nobel Chemicals, Sweden) is the type of oil tested. ARLACEL P135 (ICI, UK) in a concentration of 0.5% w/w was used as surfactant. Variations of the water/oil ratios tested were: 40/60, 50/50, 60/40 and 70/30 (all in % w/w).

Type of formalin-inactivated viral avian antigens were tested: Infectious Bronchitis (IBV), strain Massachusetts 41 (produced in eggs). The total concentration of virus suspension used was 10% w/v of the final vaccine. The aqueous phase, containing the virus suspension was diluted with 0.01 M Phosphate buffer, pH=7.2.

Preparation of the emulsions: see example 7.

Immunization of Animals

Groups of three week-old specific pathogen free (SPF) female chickens (n=8-10) were vaccinated intramuscularly with 0.5 ml of the vaccines, in the breast muscle. Blood samples for serological tests were taken on weeks 3, 6, 9 and 12 after vaccination. Virus haemagglutination inhibition (HI) tests for IBV were performed to determine the levels of antiviral serum antibody titers.

Assays for Serum Antibodies

Serum levels of IBV-specific antibodies were determined by haemagglutination inhibition assay. Serial twofold serum dilutions were prepared in microtiter plates and mixed with an equal volume containing 8 haemagglutinating units/50 µl IBV antigen. Titers were expressed as the reciprocal of the highest dilution that gives complete inhibition of haemagglutination. Samples were regarded to be positive at an inhibition of haemagglutination at dilution ≧1:16.

Results

| WATER/OIL RATIO (% w/w) | EMULSIFICATION PROCESS | 2LOG HI TITERS IBV | | | |
|---|---|---|---|---|---|
| | | 3 WKS | 6 WKS | 9 WKS | 12 WKS |
| 40/60 | High shear | 5.5 | 10.1 | 10.1 | 10.3 |
| 40/60 | Low shear | 4.1 | 10.4 | 10.9 | 9.6 |
| 50/50 | Low shear | 4.8 | 10.7 | 10.7 | 8.8 |
| 60/40 | Low shear | 6.0 | 11.1 | 9.5 | 9.8 |
| 70/30 | Law shear | 5.4 | 10.6 | 10.2 | 9.7 |

Example 9

Variation Amount of Surfactant

Materials

Ethyloleate (AKZO-Nobel Chemicals, Sweden) is the type of oil tested. The water/oil ratios tested was 40/60% w/w. ARLACEL P135 (ICI, UK) was used as surfactant. Amounts of ARLACEL P135 tested were 0.1%, 0.2%, 0.5%, 1.0%, 2.5%, 5%, 10% (all in % w/w).

Type of viral avian antigen tested was New Castle Disease Virus, strain d-12 (attenuated). The total concentration of virus suspension used was 10% w/v of the final vaccine. The aqueous phase, containing the virus suspension was diluted with 0.01 M Phosphate buffer, pH=7.2.

Preparation of the Emulsions

ARLACEL P135 is dissolved in Ethyloleate at 60° C. while stirring. After dissolution this oil phase is cooled down to room temperature. Mixing of the aqueous phase into the oil phase was performed at 1100-1300 r.p.m. using the Eurostar mixer (IKA, Germany) provided with a propeller blade. The droplet size of the emulsion was determined using interference microscopy at 1000× magnification (Olympus, model BX50, Japan). Droplet size of the emulsions was mainly 1-5 µm.

Results

These emulsions were used for in-ovo vaccination. All the emulsions showed acceptable injectability. Also the results of the hatchability test were acceptable (between 80 and 95%).

The invention claimed is:

1. An injectable, immunogenic adjuvant composition comprising a water-in-oil emulsion, wherein said emulsion comprises a vaccine antigen and a polymeric emulsifier, which is a block copolymer having a general formula A-COO-B-OOC-A, in which component B is the divalent residue of a water-soluble polyalkylene glycol and components A are the residue of an oil-soluble complex monocarboxylic acid, said emulsion having a viscosity below 450 mPas.

2. The adjuvant composition according to claim 1, characterized in that components A have a molecular weight of at least 500 and component B has a molecular weight of at least 500.

3. An adjuvant according to claim 1, characterized in that component B is derived from polyethylene glycol and components A are derived from polyhydroxystearic acid.

4. An adjuvant according to claim 1, characterized in that the polymeric emulsifier is a block copolymer of polyethylene glycol and polyhydroxystearic acid.

5. An adjuvant according to claim 1, characterized in that the emulsion comprises 0.01-15% w/w of the polymeric emulsifier.

6. An adjuvant according to claim 5, characterized in that the emulsion comprises 0.3-0.5% w/w of the polymeric emulsifier.

7. An adjuvant according to claim 1, characterized in that the oil is a metabolisable oil.

8. An adjuvant according to claim 7, characterized in that the oil is a semi-synthetic oil, or oleyl oleate.

9. An injectable, immunogenic adjuvant composition, comprising a water-in-oil-in water (w/o/w) emulsion, wherein said (w/o/w) emulsion is based on a water-in-oil emulsion comprising a vaccine antigen and a polymeric emulsifier which is a block copolymer having a general formula A-COO-B-OOC-A, in which component B is the divalent residue of a water-soluble polyalkylene glycol and components A are the residue of an oil-soluble complex monocarbxylic acid, said emulsion having a viscosity below 450 mPas.

10. The composition of claim 1, wherein the emulsion has a viscosity below 250 mPas.

11. The composition of claim 1, wherein the emulsion has a viscosity below 100 mPas.

12. The injectable adjuvant composition of claim 1, wherein the water-in-oil emulsion comprises water droplets of a size between about 1 and 5 micrometers.

13. The injectable adjuvant composition of claim 9, wherein the water-in-oil emulsion comprises water droplets of a size between about 1 and 5 micrometers.

\* \* \* \* \*